United States Patent [19]
Dolazza et al.

[11] Patent Number: 5,841,829
[45] Date of Patent: Nov. 24, 1998

[54] OPTIMAL CHANNEL FILTER FOR CT SYSTEM WITH WOBBLING FOCAL SPOT

[75] Inventors: Enrico Dolazza, Boston; Hans Weedon, Salem, both of Mass.

[73] Assignee: Analogic Corporation, Peabody, Mass.

[21] Appl. No.: 855,207

[22] Filed: May 13, 1997

[51] Int. Cl.[6] .................................................. A61B 6/03
[52] U.S. Cl. ............................ 378/4; 378/9; 378/901; 378/11
[58] Field of Search ............................ 378/4, 11, 12, 378/14, 901, 9

[56] References Cited

U.S. PATENT DOCUMENTS

| | | | |
|---|---|---|---|
| 4,547,893 | 10/1985 | Gordon | 378/19 |
| 4,689,809 | 8/1987 | Sohval | 378/136 |
| 4,819,260 | 4/1989 | Haberrecker | 378/137 |
| 4,894,850 | 1/1990 | Frings et al. | 378/62 |
| 5,065,420 | 11/1991 | Levene | 378/137 |
| 5,142,286 | 8/1992 | Ribner et al. | 341/143 |
| 5,218,533 | 6/1993 | Schanen | 378/9 |
| 5,259,014 | 11/1993 | Brettschneider | 378/138 |
| 5,265,142 | 11/1993 | Hsieh | 378/4 |
| 5,361,291 | 11/1994 | Toth et al. | 378/12 |
| 5,550,886 | 8/1996 | Dobbs et al. | 378/19 |

OTHER PUBLICATIONS

Dolazza, E., *The Bell–Spline, a Digital Filtering/Interpolation Algorithm*, Proceedings of the SPIE—The International Society For Optical Engineering SPIE Vol. 1092 Medical Imaging III: Image Processing (1989) pp. 568–583.

*Primary Examiner*—David P. Porta
*Assistant Examiner*—David Vernon Bruce
*Attorney, Agent, or Firm*—Lappin & Kusmer

[57] ABSTRACT

An improved data acquisition system filter, optimized for the time domain and for use in a computed tomography scanner of the type using x-ray focal spot wobble, includes a filter time response $F(t)$ which is a function of the waveform $w(t)$ used to drive the focal spot from one position to the other.

32 Claims, 4 Drawing Sheets

OPTIMAL CHANNEL FILTER FOR CT SYSTEM WITH WOBBLING FOCAL SPOT

FIELD OF THE INVENTION

The present invention relates generally to a data acquisition system (DAS), and more particularly, to a data acquisition system using a filter optimized for the time domain and specifically adapted for use in computed tomography (CT) scanners.

BACKGROUND OF THE INVENTION

Certain signal processing techniques involve the detection of a plurality of analog information signals for the purpose of acquiring data represented by the signals. For example, certain commercially available medical imaging systems such as CT scanners are used to image internal features of an object under view by exposing the object to a preselected amount and type of radiation. Detectors sense radiation from the object and generate analog signals representative of internal features of the object.

Figure 1:
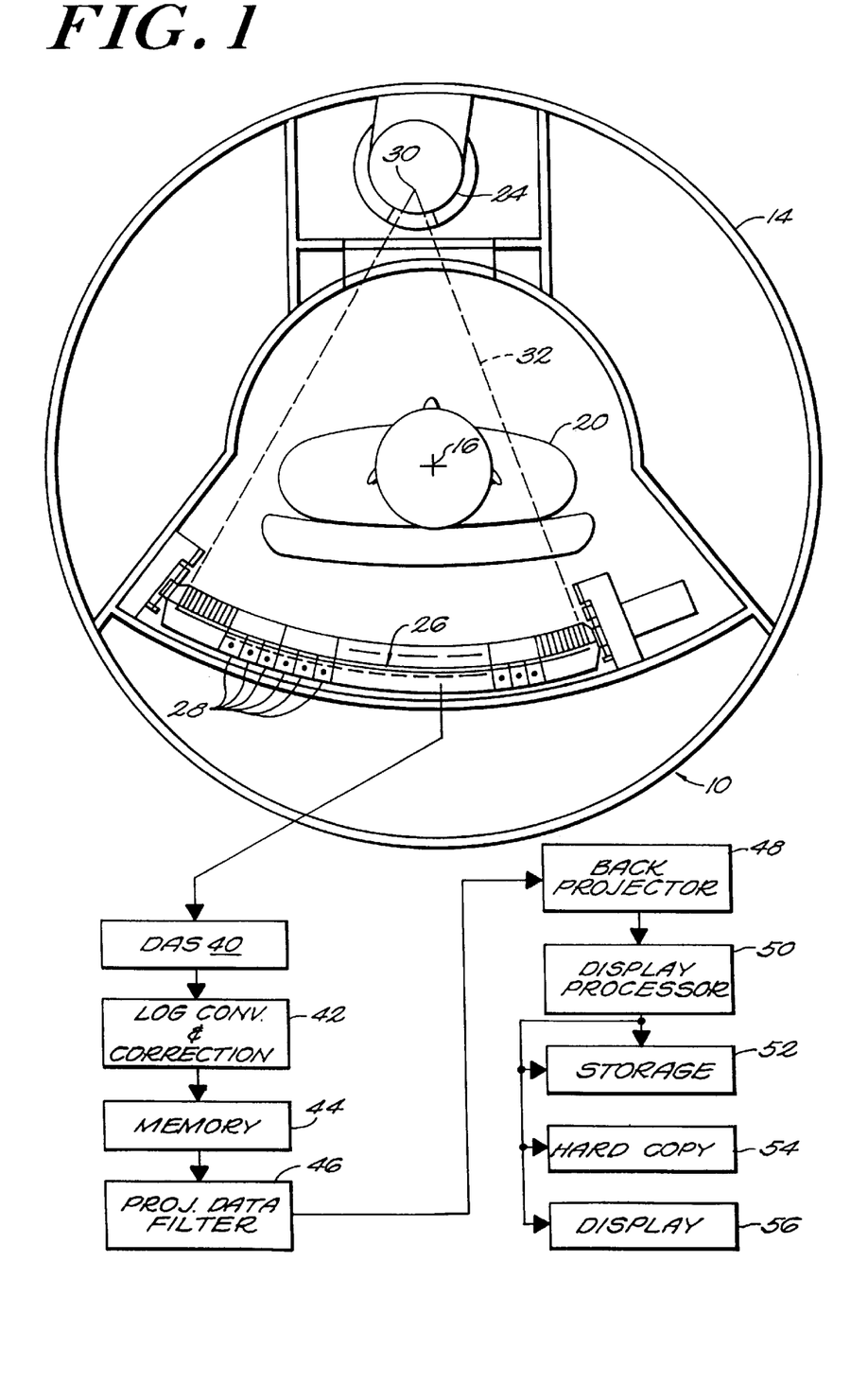
FIG. 1 is a typical third generation CT scanner of the type useful with the present invention.

In the example of CT scanners, those of the third generation type, such as the scanner 10 illustrated in FIG. 1, include an X-ray source 24 and X-ray detector system 26 secured respectively on diametrically opposite sides of an annular-shaped disk 14. The latter is rotatably mounted within a gantry support (not shown) so that during a scan the disk 14 continuously rotates about a rotation axis 16 (referred to as the "Z-axis") while X-rays pass from the source 24 through an object 20 positioned within the opening of the disk to the detector system.

The detector system 26 includes an array of detectors 28 typically disposed as a row in the shape of an arc, and spaced from a point 30, referred to as the "focal spot," where the radiation emanates from the X-ray source 24. Where the array of detectors includes a single row of detectors, the X-ray source and array of detectors are all positioned so that the X-ray paths between the source and each detector all lie in the same plane, referred to as the "scanning plane", normal to the rotation or Z-axis 16 of the disk. The X-rays that are detected by a single detector 28 at a measuring interval during a scan is considered a "ray." Because the ray paths originate from substantially a point source and extend at different angles to the detectors, the ray paths resemble a fan, and thus the term "fan" beam, indicated at 32, is frequently used to describe all of the ray paths at any one instant of time. The ray is partially attenuated by all the mass in its path so as to generate a single intensity measurement as a function of the integral of the x-ray attenuation along the path of the ray, and thus the density of the mass in that path. Projection views, i.e., the X-ray intensity measurements, are typically done at each of a plurality of angular positions of the disk. As seen in FIG. 1, the fan beam 32 created by the source 24 is directed toward the detector array 26. The detector array is connected to a DAS 40 for processing the data received from the detector array 26. In general the output of each detector is processed through a different signal channel of the DAS, although certain groups of channels may share common signal paths by using, for example, multiplexers to share common components for those channels. In general, each signal channel among other things converts the analog signal derived from the detector output into a corresponding digital signal by using an A/D converter (ADC) (not shown in FIG. 1). The digital signal is processed, as indicated generally at block 42, in a well known manner to correct for various non-linearities and errors, such as converting the signal in accordance with a log function, correcting for offset and nonlinear variations due to temperature changes, etc. The corrected data is then processed and stored in memory 44. The projection data is then filtered in accordance with a known filter function, indicated at 46, such as using a fast Fourier transform (FFT) function, multiplying the transform function by a multiplication function, and then processing the product in accordance with an inverse fast Fourier transform ($FFT^{-1}$) function. A back projection computer 48 is adapted to process the filtered data in a suitable manner using, for example, well known Radon mathematics so that the data, for example, can be provided to a display processor 50 for archival storage as indicated at 52, for providing a hard copy as indicated at 54, or for displaying on a console as indicated at 56.

For constant Z-axis scanning, an image reconstructed from data acquired at all of the projection angles during a scan will be a slice along the scanning plane through the object being scanned. For helical scanning, the scanning plane and the imaged object are translated relative to one another in the direction of the Z-axis, while the disk rotates. When the data is processed the slice plane is defined within the volume scanned. In order to "reconstruct" or "back project" a density image of the section or "slice" of the object in the defined slice plane, the image is typically reconstructed in a pixel array, wherein each pixel in the array is attributed a value representative of the attenuation of all of the rays that pass through its corresponding position in the scanning plane during a scan. As the source 24 and detectors 28 rotate around the object 20, rays penetrate the object 20 from different directions, or projection angles, passing through different combinations of pixel locations. The density distribution of the object in the slice plane is mathematically generated from these measurements, and the brightness value of each pixel is set to represent that distribution. The result is an array of pixels of differing values which represents a density image of the slice plane.

While the signals generated by the detectors through the series of readings provide the required data to generate the 2-dimensional image, acquiring and processing the data can pose various design problems. For example, a large number of detectors must be used for each set of readings taken for each projection view, and a large number of projection views must be taken during a scan in order to create a detailed image with sufficient resolution (a typical third generation CT scanner contains on the order of 350 to 1000 detectors, with, for example, 600 to 3000 projection views being taken within a period of one to two seconds resulting in data values, i.e., detector readings, on the order of one million, although these numbers can clearly vary).

Thus, each detector that acquires the X-rays from the fan beam, must spatially filter and sample the x-rays during a scan. The filter is typically a spatial integrator of linear length W (the active length of the detector along the detector array) and the sampling interval $\Delta$ is equal to the detector pitch. In general, W is very close to $\Delta$. W defines the spatial range of frequencies 0 to $f_d$ of the fan beam detectable by the array as follows:

$$f_D \leq 1/W \tag{1}$$

$\Delta$ defines the sampling frequency $f_s$ as follows:

$$f_s = 1/\Delta \tag{2}$$

As is well known, in order to prevent aliasing of the spatial frequencies of the fan beam the following must be true:

$$f_D < \frac{1}{2} f_s \qquad (3)$$

or $$f_D < \frac{1}{2\Delta} \qquad (4)$$

Thus, the filter applied to the projections must suppress spatial frequencies otherwise available to provide better resolution.

The sampling frequency of the beam, and thus the resolution of the image created, can be improved by increasing the number of detectors used and/or the sampling frequency of the fan beam. One technique which has been developed to increase the sampling rate so as to improve the resolution of a CT image is to offset the position the detector array so that it is spaced one-quarter of a detector width (or pitch) from its theoretical center. Specifically, if a line is drawn from the apex of the fan beam (the "focal spot") through the isocenter of the machine (the "isocenter" of the machine being the location within the imaging plane about which the disk rotates) to the detector array, the line will intersect one of the detectors precisely between the center and the edge of the detector. In this position the detector array acquires a set of data during the first 180° of rotation of the disk which is interleaved with the set of data acquired during the second 180° of rotation of the disk by one-half of a detector width or pitch. This has the effect of generating opposite polarity of potential aliasing artifacts that cancel in the final image generated from data taken from both directions of the object being scanned. In practice, however, this method of artifact compensation only works for stationary objects. Imaging live patients imposes an additional problem in that however still the patient remains during the scan, small motion of the tissue cancels or significantly blurs the cancellation of aliasing image artifacts. Specifically, sets of data acquired during the second 180° of rotation of the disk is interleaved with sets of data acquired during the first 180° of rotation of the disk, so that interleaved data sequentially positioned relative to one another in very close spatial relationship are not sequentially acquired in time, but over a relatively long period of time (for example, one second) where movement can cause these errors.

An alternative approach to increase resolution, which improves aliasing cancellation, is to provide the sets of interleaved data, for example corresponding to a quarter detector shift, relative to one another in a time sequence such that interleaved data sequentially positioned relative to one another in very close spatial relationship are sequentially acquired in time so that any relative movement between adjacent data would occur over a very short period of time, i.e., on the order of less than a millisecond. Thus, instead of generating two sets of interleaved data spaced 180° of rotation, the two sets of data are generated as sequentially interleaved views, therefore close in time. One such approach, called "focal spot wobbling", is described, for example in U.S. Pat. Nos. 4,689,809; 4,819,260; 4,894,850; 5,065,420 and 5,259,014, wherein instead of positioning the detector assembly in an offset position, the focal spot is modulated between two positions during the rotation of the disk at twice the rate as the rate at which projections are otherwise contemplated, so as to generate two interleaved projection sets, one corresponding to each focal spot position. Specifically, a line passing from the focal spot located in one position through the isocenter to a detector of the array positioned along that line will intersect the detector one-half the detector width from the line passing from the focal spot in the second position through the isocenter to that detector. In this manner the two sets of interleaved data acquired from the two corresponding positions of the focal spot are acquired temporally in the same sequence as they are located in the image so that aliasing cancellation is improved, and motion artifacts reduced.

For image quality, when sequentially reading the output of a signal channel of the DAS, it is clear that the reading during each sampling interval should be as independent as possible from the previous readings taken from that channel, as well as readings taken from the other channels. This affects the time domain properties of the filter that processes the channel output corresponding to the different positions of the focal spot before the signal is A/D converted. Any "spill-over" or "cross talk" of a signal in the channel from a prior sampling interval (sometimes referred to as "view-to-view cross talk"), thus will have a negative effect on the time domain properties of the converter. On the other hand, the frequency response of the A/D converter largely determines the signal-to-noise ratio and thus the quality of the signal processed through the channel. The DAS using a low pass analog filter, such as a best estimate filter of the type described in U.S. Pat. No. 4,547,893 issued Oct. 15, 1985 to Bernard M. Gordon and assigned to the present assignee, for shaping the spectral response of the output of the transimpedance amplifier is optimized for its frequency domain characteristics, at the cost of some of its time-domain properties, with spillover of as much as 25% not being unusual (i.e., 25% of the signal is from previous readings in the channel). On the other hand, an integrator type analog filter, is optimized for its time-domain characteristics, since the integrator is cleared or nulled after each sampling interval, before the next sampling interval in order to insure little or no spillover.

The time performance of the integrator filter, however, is only optimized if the focal spot is moved between the two positions instantaneously, that is the transition time between the two modulated positions should be as close to zero as possible. In this way photons can be collected alternately for one position of the focal spot followed by a second collection of photons for the second position of the focal spot, with no photons being detected during the transition between the two positions. In fact, as a practical matter there is a finite transition time when the focal spot moves between each of its two positions, and photons are necessarily detected during each such time transitional interval. There are practical reasons why a finite transitional time is necessarily a part of the implementation of such a focal spot wobbling system. The most important reason is that a finite transition is unavoidable because of the amount of reactive power required to control the deflection of the beam.

More specifically, the electron beam is modulated by passing the beam through a modulating deflection field. The modulating deflection field is necessarily driven by a modulating signal. The movement of the focal spot of the X-ray tube from one position to the next requires finite reactive energy so that the reactive power of the modulating signal increases as the transition time decreases. Thus, for example, use of a drive signal for creating the deflection field that would provide a substantially zero transition time would be practically impossible to implement, and as a practical matter would still necessarily provide a finite transition time. A drive signal in the form of a sine wave, however, which theoretically would provide transition time between successive minimum and maximum peaks of the sine wave would be more easily implemented with smaller power requirements. However, clearly, it is undesirable to discard the data associated with photons detected during the transition times, and clearly, such data contributes to create a correlation between the readings taken at different positions of the focal spot.

Thus, the DAS used to acquire data from the detectors using the focal spot wobbling technique will process data that are intrinsically not independent in time because of the portion of the data acquired during the transition times. It therefore is desirable to design the DAS filter so that it is optimized in the time domain and so that the data acquired during the transitional times will have lower impact on the determination of the values of X-ray absorption for the alternating focal spot positions with respect to data acquired at around the ideal positions of the focal spot, without significantly sacrificing the signal-to-noise ratio of the measurement.

OBJECTS OF THE INVENTION

It is an object of the present invention to reduce or substantially overcome the above-described problems associated with the prior art.

Another, more specific object of the present invention is to provide a DAS filter optimized in the time domain, i.e., the discrete separation of signals associated with the detection of x-rays in which the relative position of the source of the x-rays and the detection system is modulated between two alternating positions.

Yet another object of the present invention is to provide an improved DAS filter optimized for the time domain so as to minimize view-to-view cross talk in a focal spot wobbling system so as to increase image sharpness without compromising the signal-to-noise ratio of the measurement.

Still another object of the present invention is to provide a technique of optimizing the time domain of a DAS of a focal wobbling system, i.e., optimize the separation of discrete sets of data representing x-ray readings in corresponding positions in space resulting in modulation of the relative position of a focal spot from which the x-rays emanate and the x-ray detection system of a CT scanner regardless of the waveform used to modulate the relative position of the focal spot and the x-ray detection system.

And yet another object of the present invention is to provide improved imaging by CT scanners using a focal spot wobbling x-ray source with minimal modifications to existing systems.

SUMMARY OF THE INVENTION

The invention is directed to an improved DAS filter optimized for the time domain and having an impulse response as a function of the modulation waveform for producing the focal spot wobble. In general, the DAS filter is optimized for the time domain for each detector channel of a DAS so as to minimize the view-to-view spill over signal for each photon measurement for each view so as to maximize the separateness of the signal values corresponding to separate views, without compromise of the signal-to-noise ratio of the measurement.

In the preferred form of the invention the filter is employed in a CT scanner of the type employing a data acquisition system employing sigma-delta analog converters for generating digital data as a function of detected photons of a detector array. Such converters typically include a sigma-delta modulator and a decimator filter having a set of coefficients that describe the impulse response of the filter. The coefficients of the filter can therefore be set so as to shape the impulse response of the filter to provide an optimum trade-off between view to view separation and signal-to-noise ratio of the view measurements. The modulation waveform is preferably periodic, symmetrical or non-symmetrical, and can be of any shape, e.g., square, sawtooth, trapezoidal or sinusoidal, with a sinusoidal waveform being preferred.

In the preferred embodiment the response of the decimator filter has a central lobe closely resembling the focal spot wobbling waveform and outer lobes designed to further reduce the view to view cross talk and at the same time to reject the digitization noise of the sigma-delta modulator.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE DRAWINGS

For a fuller understanding of the nature and objects of the present invention, reference should be had to the following detailed description taken in connection with the accompanying drawings in which the same reference numerals are used to indicate the same or similar parts wherein.

DETAILED DESCRIPTION OF THE DRAWINGS

Figure 2:
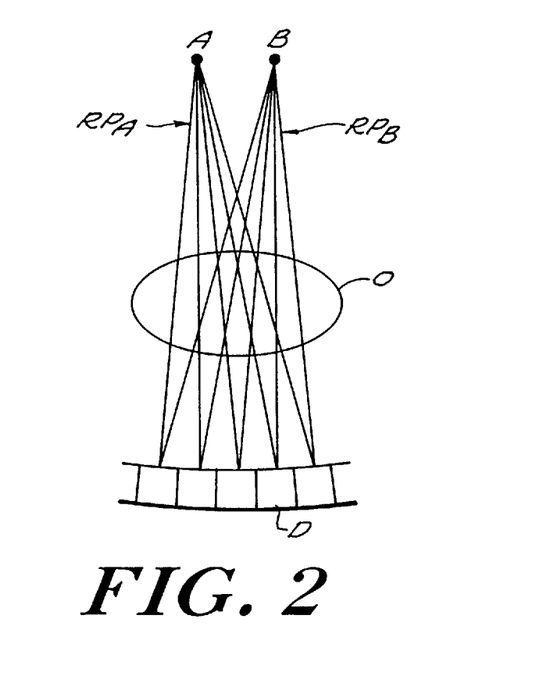
FIG. 2 is a simplified view of a focal spot wobbling x-ray source and some of the detectors of a CT scanner.

In accordance with the present invention, substantial optimum filtering for the time domain (in terms of minimizing view-to-view spill over and maximizing the signal to noise ratio) of the signal processed through each channel with each successive alternate position of the focal spot is achieved. To demonstrate both the problem posed by focal spot wobbling and solution provided by the present invention, a simplified view of a focal spot wobbling system is shown in FIG. 2. As shown, the focal spot alternately moves, or is deflected between its two primary positions, indicated at A and B, where successive projections are made. The ray path from each of the focal spot positions A and B is shown respectively as $RP_A$ and $RP_B$. During a scan, the ray paths extend from the corresponding focal spot positions through the scanned object O, to each detector, one detector being shown in FIG. 2 at D. As described in greater detail below, each detector provides a current signal as a measure of x-ray absorption along the ray path for each projection, with successive current signals from successive projections being separately processed. In a focal spot wobbling system successive projections are made when the focal spot is alternately positioned at positions A and B. For analysis purposes, theoretically the detector D generates current signal $I_A$ if the focal spot were maintained at position A for the entire projection, and current $I_B$ if the focal spot were maintained at position B for the entire projection. In general the following relationship exists:

$$I_A = k\phi_A(t) \tag{5}$$

$$I_B = k\phi_B(t) \tag{6}$$

wherein $\phi_A(t)$ and $\phi_B(t)$, both functions of time t, are the respective x-ray photon flux measurements attributed to the paths $RP_A$ and $RP_B$ during corresponding projection intervals; and k is a constant that expresses the value of the detector current for a unity amount of photon flux.

It should be appreciated that $$I(t)dt=k\phi(t)dt=dn(t) \tag{7}$$

wherein dn(t) is the number of photons detected in the time dt, when the signal I(t) is observed.

In practice, the current signal generated by the detector D will be continuous, and will necessarily include the combination of these two currents during the transition time.

Figure 3:
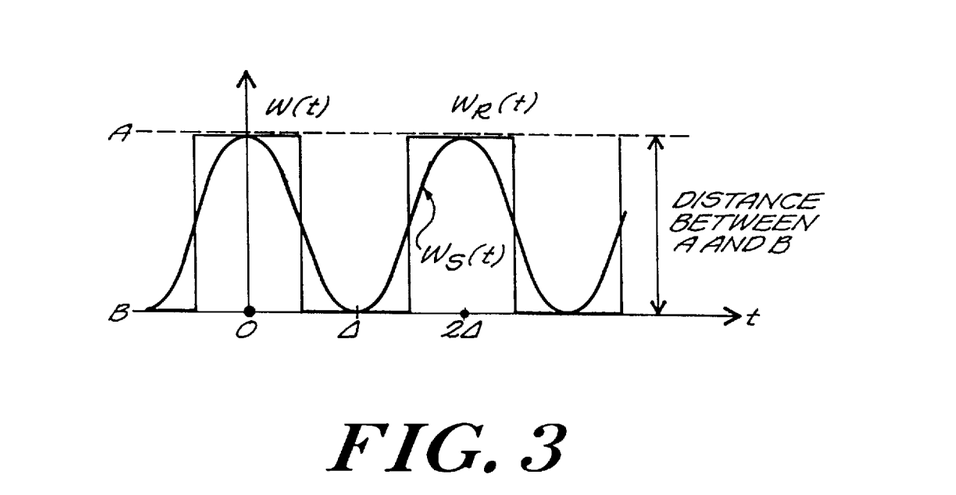
FIG. 3 is a graphical illustration of examples of waveforms used to drive the deflection field of a focal spot wobbling CT system.

Referring to FIG. 3, the distance between positions A and B is indicated on the vertical axis between the maximum and minimum values, while time is indicated on the horizontal axis. For purposes of illustration the motion of the focal spot between positions A and B is assumed for analysis purposes to be either a square wave function, indicated as the function $w_R(t)$, or as sinusoidal function $w_S(t)$, but it should be understood that the waveform can take other forms and is generally referred to herein as the waveform function w(t). The signal of the detector D, designated G(t), is therefore initially defined as a function of the waveform w(t) (which defines the movement of the focal spot), so that G(t) is defined as follows:

$$G(t)=k\phi_A(t)w(t)+k\phi_B(t)[1-w(t)] \tag{8}$$

It is assumed that during each cycle of w(t) one filters and samples the values of G(t) intervals at time $j\Delta$, where j is an integer and $\Delta$ is the time difference between the two time instances when the focal spot is precisely and successively positioned at the points A and B. For the sinusoidal function $w_s(t)$, the samples are taken respectively when the focal spot is precisely positioned at points A (when w(t)=A) and B (when w(t)=B), i.e., when the sinusoidal motion of the focal spot reaches the ideal points A and B.

In accordance with the invention, and as will be more clearly understood hereinafter, the signal G(t) is filtered in time with the filter function F(t) to create the signal $S(\tau)$ sampled synchronously with the movement of the focal spot. The signal $S(\tau)$ is therefore convolved from $G(\tau-t)$ and F(t), or $$S(\tau)=\int G(\tau-t)F(t)dt \tag{9}$$

The following assumptions, which are reasonable assumptions, are made for the purpose of further mathematical analysis:

$\phi(t)$ varies slowly with respect to w(t), i.e., the movement of the focal spot is at a high frequency rate when compared to changes in the flux along a ray path from one view to the next; and, w(t) is symmetrical around the sampling time (although it should be appreciated that non-symmetrical waveforms, such as a sawtooth wave function can be used, although the following analysis will be different).

Since it can be reasonably assumed that $\phi$ is changing very slowly from one view to the next, one can use the average value of $\phi$ (hereinafter designated $\overline{\phi}$) for each corresponding view, since it can be assumed that the flux reading does not vary significantly from view to view, and therefore can be reasonably approximated to a constant in each sample so that the following can be derived from Equation (9):

$$S(\tau) \approx k\overline{\phi_{A,\tau}} \int w(\tau-t)F(t)dt + k\overline{\phi_{B,\tau}} \int [1-w(\tau-t)]F(t)dt \tag{10}$$

At time $\tau=0$, the sample value $S(\tau=0)$ is give by:

$$S(0) \approx k\overline{\phi_{A,0}} \int w(t)F(t)dt + k\overline{\phi_{B,0}} \int [1-w(t)]F(t)dt \tag{11}$$

It should be noted that in Equation (11), w(-t)=w(t) because the waveform has been considered to be symmetrical about 0. It is also noted that while $\phi_{A,0}$ and $\phi_{B,0}$ are considered constant for the sampling period and approximated to their average values $\overline{\phi_{A,0}}$ and $\overline{\phi_{B,0}}$ for each sampling period, the constant values clearly can vary from sample to sample without affecting the current analysis.

It is further assumed that the filter input response is non-zero over a relatively small time interval, i.e., it has only a significant value around where the signal sample is. Thus, the following hypothesis is adopted that the value of F(t) is substantially $\neq 0$ only when $|t| \leq 1.5\Delta$, or $-1.5\Delta < t < +1.5\Delta$, i.e., for three $\Delta$ intervals. In addition, the following can be stated about the function w(t) in the same interval $|t| \leq 1.5\Delta$:

$$1-w(t)=w(t+\Delta)+w(t-\Delta) \tag{12}$$

because $w(t)+w(t+\Delta)+w(t-\Delta)$ must be equal to 1 over the interval.

Substituting Equation (12) into Equation (11), the latter becomes:

$$S(0) \approx k\overline{\phi_{A,0}} \int w(t)F(t)dt + k\overline{\phi_{B,0}} \int [w(t+\Delta)+w(t-\Delta)]F(t)dt \tag{13}$$

The first term of Equation (13) is the amount of the wanted signal and the second term is the amount of the unwanted signal that are combined in the value of the sample S(0) taken at $\tau=0$. One can define a figure of merit $\epsilon$ of the spill-over that is a function of the motion of the focal spot defined by w(t) and of the channel filter defined by F(t) as the ratio of the amount of the unwanted signal and of the wanted signal, both normalized for their respective average photon fluxes. Accordingly, $$\xi = \frac{\int [w(t+\Delta)+w(t-\Delta)] \cdot F(t)dt}{\int w(t) \cdot F(t)dt} \tag{14}$$

An appropriate figure of merit $\epsilon$ of the signal to noise ratio of the measurement is the ratio between the amount of wanted signal combined in the value of the sample and the overall sample rms (root mean square) value of the photon noise due to both the wanted and the unwanted signal.

The amount of the wanted signal $S_A$ combined in the value of the sample is the first term of equation (11):

$$S_A = k\overline{\phi_{A,0}} \int w(t) \cdot F(t)dt \tag{15}$$

To evaluate the overall sample noise due to both wanted and unwanted photons, it is reasonable to introduce the further hypothesis that $\overline{\phi_{A0}}$ and $\overline{\phi_{B0}}$, being close to one another, can be approximated to the same value $\overline{\phi_0}$ for the purpose of estimating the sample noise. Under this hypothesis equation (8) becomes:

$$G(t)dt = k\phi_A(t)w(t) + k\phi_B(t)[1-w(t)] = \overline{k\phi_0} \quad (16)$$

The resulting photon noise associated with the sample, therefore, has a variance $v$ and a standard deviation $\sigma$ given by the following:

$$v = \sigma^2 = \int G^2(t)F^2(t)dt = \overline{k^2\phi_0^2} \int F^2(t)dt \quad (17)$$

and $$\sigma = \overline{k\phi_0}\sqrt{\int F^2(t)dt} \quad (18)$$

In conclusion, the figure of merit of the signal to noise ratio of the measurement is given by:

$$\frac{S_A}{\sigma} = \frac{k\overline{\phi_{A,0}}\int w(t) \cdot F(t)dt}{\overline{k\phi_0}\sqrt{\int F^2(t)dt}} \approx \frac{\int w(t) \cdot F(t)dt}{\sqrt{\int F^2(t)dt}} \quad (19)$$

It will be evident from Equations (14) and (19) that both the spill-over and the signal to noise ratio are each a function of both F(t) and w(t), and that given w(t) it is possible to find a F(t) that optimally trades off the two parameters, and that the impulse response of the filter optimally chosen would be as close as possible to the waveform function that defines the motion of the focal spot for maximizing the signal to noise ratio. From these equations it is evident that when the focal spot moves instantaneously from A to B the integrating filter is the best filter from a viewpoint of both the spillover and the signal to noise ratio.

Figure 4:
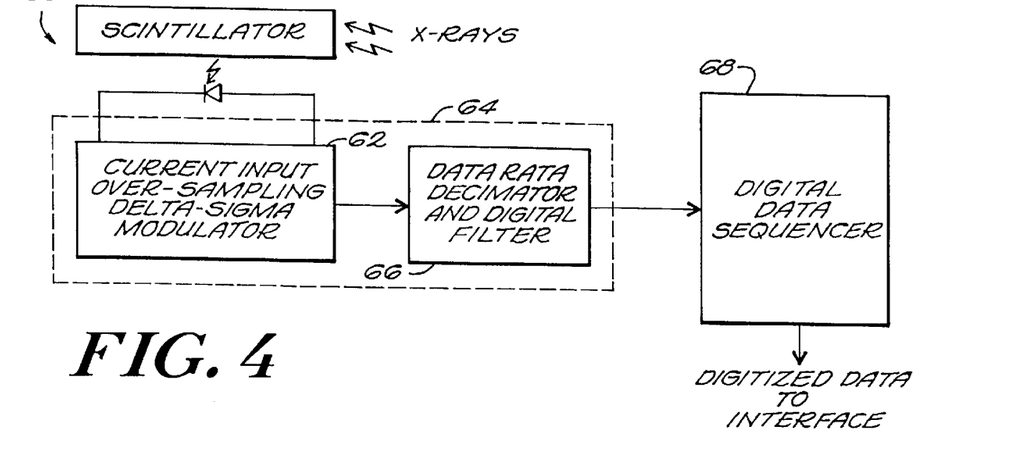
FIG. 4 is a block diagram of one type of detector which can employ the present invention.

Thus, it is desirable to construct a filter with a shape that provides the optimal tradeoff. In general, optimally filtered samples can be obtained by oversampling the signal and properly weighting the oversamples. In oversampling processes, the number of bits/sample can then be reduced to a limit of one by properly shaping the spectrum of the digitization noise. This can work well with a delta-sigma converter, such as described in co-pending application, U.S. application Ser. No. 08/12137, filed on Sep. 11, 1996 (ANA-64FWC), which is a continuation of U.S. application Ser. No. 08/326276, filed on Oct. 20, 1994 and now abandoned, both applications being filed in the names of Bernard M. Gordon, Hans Weedon and Louis R. Poulo and entitled Data Acquisition System Using Delta-Sigma Analog-to-Digital Signal Converters, the applications being incorporated herein by reference. Such a delta-sigma analog-to-digital signal converter is shown in FIG. 4. As shown in FIG. 4, the current output of the detector D, shown as a diode 60 where the detector is a solid state detector (although it should be appreciated that other types of detectors are known, such as gas detectors), is applied directly to the input of the current input, oversampling delta-sigma modulator 62 of the delta-sigma A/D converter 64. The output of the modulator is applied to the data rate decimator and digital filter 66, for reducing the data rate to within the bandwidth of interest and for filtering out high frequency noise. The output of the filter 66 is applied to the digital filter and data sequencer 68. The digital filter and decimator is preferably a finite impulse response (FIR) filter having predetermined coefficients stored in read only memory (ROM) for setting the taps of the filter, as described in the co-pending application. The filter function F(t) can easily be shaped by setting the tap values depending upon the waveform w(t) in a manner for the number of cycles desired. In the preferred embodiment the response of the decimator filter has a central lobe closely resembling the focal spot wobbling waveform and outer lobes designed to reduce the view to view spillover, as well as the high frequency noise of the modulator output. In one embodiment, the value of the filter function F(t) is substantially $\neq 0$ only for three cycles, i.e., $3\Delta$, adopting the suggested hypothesis described above, i.e., the value of F(t) is substantially$\neq 0$ only when $|t| \leq 1.5\Delta$, or $-1.5\Delta < t < +1.5\Delta$. It should be evident, however, that the present invention can be employed with other types of filter including other types of digital filters and/or other types of digital types of signal converters (such as the filters and delta-sigma analog-to-digital signal converters described in U.S. Pat. No. 5,142,286 issued in the names of David B. Ribner and Michael A. Wu for Read-out Photodiodes Using Delta-Sigma Oversampled Analog-to-Digital Converters) as well as analog filters, such as integrating filters.

EXAMPLE #1

The waveform for moving the focal spot between the position A and position B is defined as follows:

$$w(t) = \begin{cases} 1 - 2t^2/\Delta^2 & \text{when } |t| \leq \frac{\Delta}{2} \\ 2 - 4t/\Delta + 2t^2/\Delta^2 & \text{when } \frac{\Delta}{2} \leq |t| \leq \Delta \\ 0 & \text{everywhere else} \end{cases}$$

This waveform defines a drive signal of substantially constant acceleration. Using an integrator filter, $$F_1(t) = \begin{cases} \frac{1}{\Delta} & \text{when } |t| \leq \frac{\Delta}{2} \\ 0 & \text{everywhere else} \end{cases}$$

Then, $$\left(\frac{S_A}{\sigma}\right)_1 = \sqrt{\overline{\phi_0}} \; 5 \frac{\sqrt{\Delta}}{6} = 0.833\sqrt{\Delta\overline{\phi_0}},$$

and $$\xi_1 = 0.20$$

EXAMPLE #2

Figure 5:
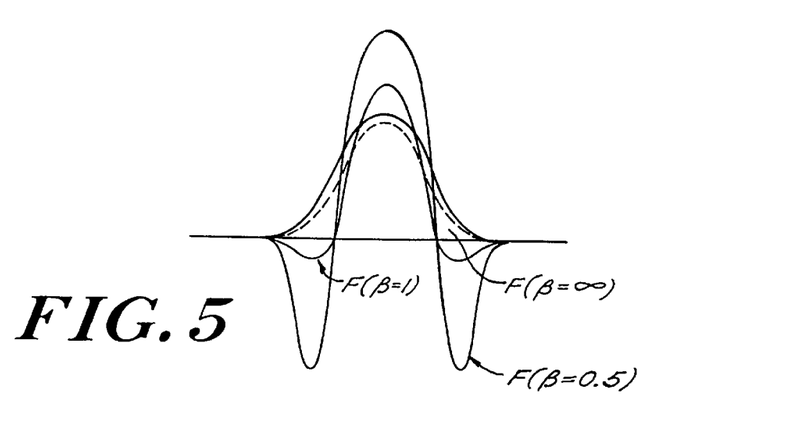
FIG. 5 shows various time responses of filters according to one example of the present invention.

Using a different type of filter, also similar to w(t) and having a Bell-Spline impulse response, is described in Dolazza, Dr. Ing. Enrico, "The Bell-Spline, a Digital Filtering/Interpolation Algorithm" *Proceedings of the SPIE=The International Society for Optical Engineering*, SPIE Volume 1092 Medical Imaging III: Image Processing (1989), pp. 568–583, and can be analytically described as follows:

$$F_2(t) = \begin{cases} \frac{24t^3}{\beta\Delta^4} - \frac{2(9+\beta)t^2}{\beta\Delta^3} + \frac{(\beta+1)}{\beta\Delta} & \text{when } |t| \leq \frac{\Delta}{2} \\ -\frac{8t^3}{\beta\Delta^4} - \frac{2(9+\beta)t^2}{\beta\Delta^3} - \frac{4(\beta+3)t}{\beta\Delta^2} + \frac{2(\beta+1)}{\Delta\beta} & \text{when } \frac{\Delta}{2} \leq |t| \leq \Delta \\ 0 & \text{everywhere else} \end{cases}$$

wherein β is a parameter that weights the spline function with the bells function, as described in the above-referenced publication. In FIG. 5, the filter kernel is shown for different values of β. Then $$\left(\frac{S_A}{\sigma}\right)_2 = \sqrt{\phi_0 \Delta} \frac{13 + 46\beta}{\sqrt{120}\sqrt{23\beta^2 + 13\beta + 90/7}},$$

and $$\xi = \frac{-13 + 14\beta}{13 + 46\beta}$$

Figure 6:
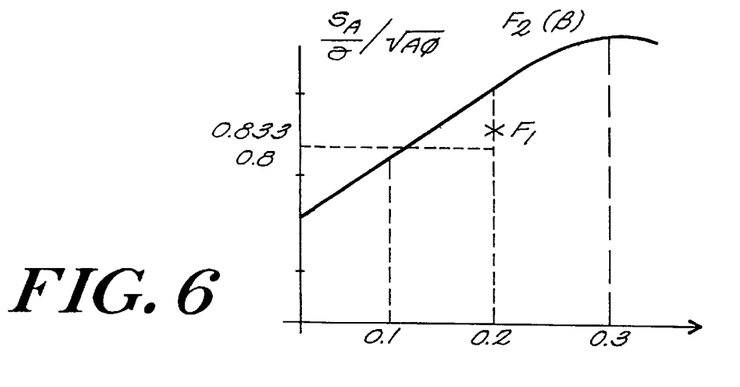
FIG. 6 is a graphical illustration of a comparison of the sample to sample spill over and of the sample signal to noise ratio of examples of types of filters which can be made in accordance with the present invention.

FIG. 6 compares the figures of merit for the signal to noise ratio $S_A/\tau$ and for the spillover $\epsilon$ for the two examples. In FIG. 6 the figures of merit for the filter $F_1$ are two numbers:

$$(S_A/\sigma)/\sqrt{\Delta\overline{\phi_0}} = 0.833,$$

and $$\xi = 0.2;$$

whereas the figures of merit for the filter $F_2$ are the coordinate of the points corresponding to different values of the parameter β.

FIG. 6 shows that for the case of the w(t) considered in the example, the filter $F_2$ yields better results than the integrator filter $F_1$ in the sense that at the same level of the signal to noise ratio, $F_2$ provides less view to view cross talk and at the same level of cross talk $F_2$ provides better signal to noise ratio.

Figure 7:
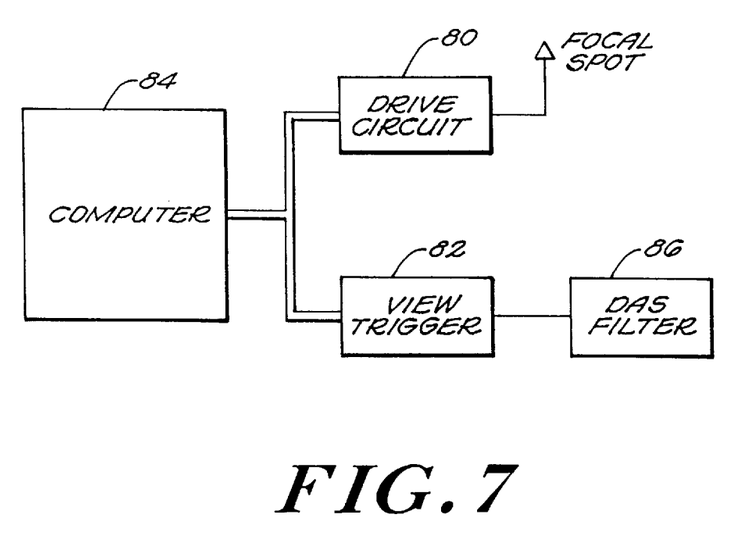
FIG. 7 is an implementation of the use of the filter in a CT scanner such as the one shown in FIG. 1.

FIG. 7 shows an implementation for synchronizing the waveform w(t) with the filter function F(t). As shown, the drive circuit 80 for deflecting the beam so that the beam moves between points A and B, and the view trigger 82 for indicating when a measuring interval for a view is commenced are both controlled by the scanner computer 84. The parts can be mounted directly on the disk 14 (shown in FIG. 1). The output of the view trigger is connected to the filter 86 of the DAS so the timing of the drive function w(t) provided by the drive circuit 80 is synchronized with the filter function F(t).

The invention thus provides for a DAS filter optimized for the time domain, i.e., the discrete separation of signals associated with the detection of x-rays in which the relative position of the source of the x-rays and the detection system is modulated between two alternating positions so as to minimize view-to-view cross talk, and provide maximum signal to noise ratio. The invention is particularly useful in improving the image quality in terms of both resolution and noise in CT systems employing focal spot wobbling. In fact, the invention provides for the optimization of the separation of discrete sets of data representing x-ray readings in corresponding positions in space resulting in modulation of the relative position of a focal spot from which the x-rays emanate and the x-ray detection system of a CT scanner regardless of the waveform used to modulate the relative position of the focal spot and the x-ray detection system. The further advantage is that the invention provides for improved imaging by CT scanners using a focal spot wobbling x-ray source with minimal modifications to existing systems. Other modifications and implementations will occur to those skilled in the art without departing from the spirit and the scope of the invention as claimed. Accordingly, the above description is not intended to limit the invention except as indicated in the following claims.

What is claimed is:

1. A data acquisition system of the type for use in a CT scanner including (a) means for defining a focal spot of an x-ray source, and (b) means for shifting the focal spot between at least two positions in accordance with a function w(t) so as to acquire sample measurements with respect to ray paths during a scan defined by the positions of the focal spot during the views of the scan, said system comprising:
   at least one detector for generating a signal G(t) in response to the sample measurements acquired during a scan; and
   filter means for filtering the signal G(t) and having a time response F(t) as a function of w(t).

2. A data acquisition system according to claim 1, wherein F(t) is a function of w(t) so as to reduce view-to-view spill over of the sample measurements and improve the signal to noise ratio s/τ of the sample measurements.

3. A data acquisition system according to claim 2, wherein the view to view spill over is measured by a figure of merit $\epsilon$ as the amount of wanted signal and the amount of unwanted that are combined in the value of each sample measurement.

4. A data acquisition system according to claim 3, wherein $$\xi = \frac{\int [w(t+\Delta) + w(t-\Delta)] \cdot F(t)dt}{\int w(t) \cdot F(t)dt}$$

5. A data acquisition system according to claim 2, wherein the signal to noise ratio is measured by a figure of merit equal to the ratio between the amount of wanted signal combined in the value of the sample measurement and the overall sample measurement rms (root mean square) value of the photon noise due to both the wanted and the unwanted signal.

6. A data acquisition system according to claim 5, wherein the signal to noise ratio $S_A/\tau$ for a sample measurement $S_A$ corresponding to the focal spot at a position A is defined as:

$$\frac{S_A}{\sigma} = \frac{k\overline{\phi_{A,0}} \int w(t) \cdot F(t)dt}{k\overline{\phi_0}\sqrt{\int F^2(t)dt}} \approx \frac{\int w(t) \cdot F(t)dt}{\sqrt{\int F^2(t)dt}},$$

wherein k is a constant;
$\overline{\phi_{A,0}}$ is the average measured flux value corresponding to the focal spot positon A for a sampling period; and
$\overline{\phi_0}$ is the average measured flux value for the entire sample measurement.

7. A data acquisition system according to claim 1, wherein F(t) is a function of w(t) so as to optimize view-to-view signal separation of the sample measurements and the signal to noise ratio s/τ of the sample measurement.

8. A data acquisition system according to claim 1, wherein w(t) is a periodically varying function with a cycle time equal to Δ.

9. A data acquisition system according to claim 8, wherein w(t) is a symmetrically time varying signal used to move the focal spot between said positions.

10. A data acquisition system according to claim 9, wherein w(t) is a sine waveform.

11. A data acquisition system according to claim 9, wherein w(t) is a square waveform.

12. A data acquisition system according to claim 9, wherein w(t) is a trapezoidal waveform.

13. A data acquisition system according to claim 9, wherein the filter means is an integrating filter, and w(t) is a signal for providing constant acceleration of said focal spot as said focal spot moves between the two positions.

14. A data acquisition system according to claim 8, wherein w(t) is a non-symmetrically time varying signal used to move the focal spot between said positions.

15. A data acquisition system according to claim 14, wherein w(t) is a sawtooth waveform.

16. A data acquisition system according to claim 1, wherein said filter means includes a filter for defining a bell-spline impulse response.

17. A CT scanner comprising:
 (a) means for defining a focal spot of an x-ray source;
 (b) means for shifting the focal spot between at least two positions in accordance with a function w(t) so as to acquire samples with respect to ray paths during a scan defined by the positions of the focal spot during the views of the scan;
 (c) at least one detector for generating a signal G(t) in response to the samples acquired during a scan; and
 (d) filter means for filtering the signal G(t) and having a time response F(t) as a function of w(t).

18. A scanner according to claim 17, wherein F(t) is a function of w(t) so as to reduce view-to-view spill over of the sample measurements and improve the signal to noise ratio s/τ of the sample measurements.

19. A scanner according to claim 18, wherein the view to view spill over is measured by a figure of merit ε as the amount of wanted signal and the amount of unwanted that are combined in the value of each sample measurement.

20. A scanner according to claim 19, wherein $$\xi = \frac{\int [w(t+\Delta) + w(t-\Delta)] \cdot F(t)dt}{\int w(t) \cdot F(t)dt}$$

21. A scanner according to claim 18, wherein the signal to noise ratio is measured by a figure of merit equal to the ratio between the amount of wanted signal combined in the value of the sample measurement and the overall sample measurement rms (root mean square) value of the photon noise due to both the wanted and the unwanted signal.

22. A scanner according to claim 21, wherein the signal to noise ratio $S_A/\tau$ for a sample measurement $S_A$ corresponding to the focal spot at a position A is defined as:

$$\frac{S_A}{\sigma} = \frac{k\overline{\phi_{A,0}} \int w(t) \cdot F(t)dt}{k\overline{\phi_0}\sqrt{\int F^2(t)dt}} \approx \frac{\int w(t) \cdot F(t)dt}{\sqrt{\int F^2(t)dt}},$$

wherein k is a constant;

$\overline{\phi_{A,0}}$ is the average measured flux value corresponding to the focal spot positon A for a sampling period; and $\overline{\phi_0}$ is the average measured flux value for the entire sample measurement.

23. A scanner according to claim 17, wherein F(t) is a function of w(t) so as to optimize view-to-view signal separation of the sample measurements and the signal to noise ratio s/τ of the sample measurement.

24. A scanner according to claim 17, wherein w(t) is a periodically varying function with a cycle time equal to Δ.

25. A scanner according to claim 24, wherein w(t) is a symmetrically time varying signal used to move the focal spot between said positions.

26. A scanner according to claim 25, wherein w(t) is a sine waveform.

27. A scanner according to claim 25, wherein w(t) is a square waveform.

28. A scanner according to claim 25, wherein w(t) is a trapezoidal waveform.

29. A scanner according to claim 17, wherein the filter means is an integrating filter, and w(t) is a signal for providing constant acceleration of said focal spot as said focal spot moves between the two positions.

30. A scanner according to claim 24, wherein w(t) is a non-symmetrically time varying signal used to move the focal spot between said positions.

31. A scanner according to claim 30, wherein w(t) is a sawtooth waveform.

32. A scanner according to claim 17, wherein said filter means includes a filter for defining a bell-spline impulse response.

* * * * *